(12) United States Patent
Delis et al.

(10) Patent No.: US 8,415,443 B2
(45) Date of Patent: *Apr. 9, 2013

(54) HYDROSILYLATION CATALYSTS

(75) Inventors: Johannes G. P. Delis, Bergen op Zoom (NL); Paul J. Chirik, Ithaca, NY (US); Aaron M. Tondreau, Ithaca, NY (US)

(73) Assignees: Momentive Performance Materials Inc., Waterford, NY (US); Cornell University, Ithaca, NY (US)

( * ) Notice: Subject to any disclaimer, the term of this patent is extended or adjusted under 35 U.S.C. 154(b) by 244 days.

This patent is subject to a terminal disclaimer.

(21) Appl. No.: 12/832,533

(22) Filed: Jul. 8, 2010

(65) Prior Publication Data

US 2011/0009565 A1    Jan. 13, 2011

Related U.S. Application Data

(60) Provisional application No. 61/224,609, filed on Jul. 10, 2009.

(51) Int. Cl.
*C08G 77/06* (2006.01)
(52) U.S. Cl.
USPC ............ 528/14; 502/150; 502/162; 502/167; 502/402; 502/405; 502/406; 502/414; 528/21; 528/31; 528/32
(58) Field of Classification Search .................... None
See application file for complete search history.

(56) References Cited

U.S. PATENT DOCUMENTS

| | | | |
|---|---|---|---|
| 3,159,601 A | 12/1964 | Ashby | |
| 3,220,972 A | 11/1965 | Lamoreaux | |
| 3,775,452 A | 11/1973 | Karstedt | |
| 5,955,555 A | 9/1999 | Bennett | |
| 6,461,994 B1 | 10/2002 | Gibson et al. | |
| 6,657,026 B1 | 12/2003 | Kimberley et al. | |
| 7,053,020 B2 | 5/2006 | De Boer et al. | |
| 7,148,304 B2 | 12/2006 | Kimberley et al. | |
| 7,442,819 B2 | 10/2008 | Ionkin et al. | |

FOREIGN PATENT DOCUMENTS

| | | |
|---|---|---|
| WO | WO02/088289 | 11/2002 |
| WO | WO2010/016416 | 2/2010 |

OTHER PUBLICATIONS

Abstract for "Electrochemistry and Spectroscopy of Organometallic Terpyridine Nickel Complexes" authored by Hamacher et al. and published in Inorg. Chem. (2009) 48(20), 9947-9951.*
Abstract for "Ligand Redox Effects in the Synthesis, Electronic Structure, and Reactivity of an Alkyl-alkyl Cross Coupling Catalyst" authored by Jones et al. and published in JACS (2006) 128(40), 13175-13183.*
Kuo, Yang Ming, Jiemian Kexue Huizhi (Journal of the Chinese Colloid and Interface Society), 15(1), 23-43.
Speier, J.L., Webster J.A. and Barnes G.H., J. Am. Chem. Soc. 79, 794 (1957).
Nesmeyanov. A.N. et al., Tetrahedron 1962, 17, 61.
Corey, J.Y. et al., J. Chem. Rev. 1999, 99, 175.
C. Randolph, M.S. Wrighton, J. Am. Chem. Soc. 108 (1986) 3366.
Bart et al., J. Am. Chem. Soc., 2004, 126, 13794.
Andrew M. Archer et al., Organometallics, 2006, 25, 4269.
Macromol. Chem. Phys. 2001, 202, No. 5, pp. 645-653.
Glatz et al., Journal of Chromatography A, 1015 (2003) 65-71.
Kim et al., Journal of Organometallic Chemistry 673 (2003) 77-83.
Chen, H. et al., Inorganic Chemistry, 2005, pp. 7661-7670.
Yeung, C.-T., et al., Inorganica Chimica Acta, Jul. 1, 2009, pp. 3267-3273.

* cited by examiner

*Primary Examiner* — Marc Zimmer
(74) *Attorney, Agent, or Firm* — Dominick G. Vicari; Joseph S. Ostroff; Wiggin and Dana LLP

(57) ABSTRACT

Disclosed herein are metal-terpyridine complexes and their use in hydrosilylation reactions.

16 Claims, No Drawings

HYDROSILYLATION CATALYSTS

CROSS-REFERENCE TO RELATED APPLICATION

This application claims priority to U.S. provisional application No. 61/224,609, filed Jul. 10, 2009, which is herein incorporated by reference in its entirety.

FIELD OF THE INVENTION

This invention relates generally to transition metal-containing compounds, more specifically to manganese, iron, cobalt, or nickel complexes containing terpyridine ligands and their use as efficient and selective hydrosilylation catalysts.

BACKGROUND OF THE INVENTION

Hydrosilylation chemistry, typically involving a reaction between a silyl hydride and an unsaturated organic group, is the basis for synthesis routes to produce commercial silicone-based products like silicone surfactants, silicone fluids and silanes as well as many addition cured products like sealants, adhesives, and silicone-based coating products. Heretofore, hydrosilylation reactions have been typically catalyzed by precious metal catalysts, such as platinum or rhodium metal complexes.

Various precious metal complex catalysts are known in the art. For example, U.S. Pat. No. 3,775,452 discloses a platinum complex containing unsaturated siloxanes as ligands. This type of catalyst is known as Karstedt's-catalyst. Other exemplary platinum-based hydrosilylation catalysts that have been described in the literature include Ashby's catalyst as disclosed in U.S. Pat. No. 3,159,601, Lamoreaux's catalyst as disclosed in U.S. Pat. No. 3,220,972, and Speier's catalyst as disclosed in Speier, J. L., Webster J. A. and Barnes G. H., J. Am. Chem. Soc. 79, 974 (1957).

Although these precious metal complex catalysts are widely accepted as catalysts for hydrosilylation reactions, they have several distinct disadvantages. One disadvantage is that the precious metal complex catalysts are inefficient in catalyzing certain reactions. For example, in the case of hydrosilylations of allyl polyethers with silicone hydrides using precious metal complex catalysts, use of an excess amount of allyl polyether, relative to the amount of silicone hydride, is needed to compensate for the lack of efficiency of the catalyst in order to ensure complete conversion of the silicone hydride to a useful product. When the hydrosilylation reaction is completed, this excess allyl polyether must either be: (A) removed by an additional step, which is not cost-effective, or (B) left in the product which results in reduced performance of this product in end-use applications. Additionally, the use of an excess amount of allyl polyether typically results in a significant amount of undesired side products such as olefin isomers, which in turn can lead to the formation of undesirably odoriferous by-product compounds.

Another disadvantage of the precious metal complex catalysts is that sometimes they are not effective in catalyzing hydrosilylation reactions involving certain type of reactants. It is known that precious metal complex catalysts are susceptible to catalyst poisons such as phosphorous and amine compounds. Accordingly, for a hydrosilylation involving unsaturated amine compounds, the precious metal catalysts known in the art are normally less effective in promoting a direct reaction between these unsaturated amine compounds with Si-hydride substrates, and will often lead to the formation of mixtures of undesired isomers.

Further, due to the high price of precious metals, the precious metal-containing catalysts can constitute a significant proportion of the cost of silicone formulations. Recently, global demand for precious metals, including platinum, has increased, driving prices for platinum to record highs, creating a need for effective, low cost replacement catalysts.

As an alternative to precious metals, recently, certain iron complexes have gained attention for use as hydrosilylation catalysts. Illustratively, technical journal articles have disclosed that that $Fe(CO)_5$ catalyzes hydrosilylation reactions at high temperatures. (Nesmeyanov, A. N. et al., Tetrahedron 1962, 17, 61), (Corey, J. Y. et al., J. Chem. Rev. 1999, 99, 175), (C. Randolph, M. S. Wrighton, J. Am. Chem. Soc. 108 (1986) 3366). However, unwanted by products such as the unsaturated silyl olefins, which are resulted from dehydrogenative silylation, were formed as well.

A five-coordinate Fe(II) complex containing a pyridine di-imine (PDI) ligand with isopropyl substitution at the ortho positions of the aniline rings has been used to hydrosilate an unsaturated hydrocarbon (1-hexene) with primary and secondary silanes such as $PhSiH_3$ or $Ph_2SiH_2$ (Bart et al., J. Am. Chem. Soc., 2004, 126, 13794) (Archer, A. M. et al. Organometallics 2006, 25, 4269). However, one of the limitations of these catalysts is that they are only effective with the aforementioned primary and secondary phenyl-substituted silanes, and not with, for example, tertiary or alkyl-substituted silanes such as $Et_3SiH$, or with alkoxy substituted silanes such as $(EtO)_3SiH$.

Other metal-PDI complexes have also been disclosed in U.S. Pat. Nos. 5,955,555, 6,461,994, 6,657,026, 7,053,020, 7,148,304 and 7,442,819. However, the catalysts and catalyst systems disclosed in these references are described for use in the context of olefin polymerizations and/or oligomerisations, not in the context of hydrosilylation reactions.

Certain other tridentate metal complexes are also known in the prior art. For example, WO 02/088289 discloses metal-terpyridine complexes. However, the publication focuses on the use of these metal complexes as oxidation catalysts, especially for improving the action of peroxide in the treatment of textile materials. No other uses for these complexes are disclosed or suggested.

As such, it is appreciated that there is a continuing need in the hydrosilation industry for non-precious metal-based catalysts that are effective for selectively and efficiently catalyzing hydrosilylation reactions. The present invention provides one answer to that need.

SUMMARY OF THE INVENTION

In one aspect, the present invention provides a complex of Formula (I):

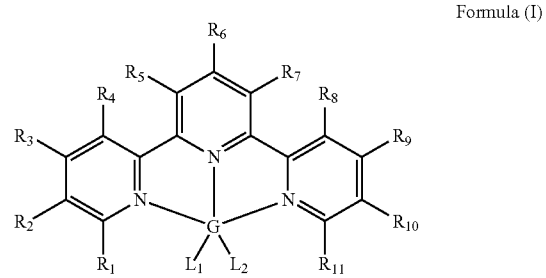

Formula (I)

wherein:

G is Mn, Fe, Ni or Co;

$R_1$, $R_2$, $R_3$, $R_4$, $R_5$, $R_6$, $R_7$, $R_8$, $R_9$, $R_{10}$ and $R_{11}$ are independently hydrogen, C1-C18 alkyl, C1-C18 substituted alkyl, aryl, substituted aryl, or an inert functional group, wherein $R_1$-$R_{11}$, other than hydrogen, optionally contain at least one heteroatom; and wherein optionally $R_4$ and $R_5$ and/or $R_7$ and $R_8$ are joined together to form a ring being a substituted or unsubstituted, saturated, or unsaturated cyclic or polycyclic ring structure; and $L_1$ and $L_2$ are independently C1-C18 alkyl, C1-C18 substituted alkyl, aryl or substituted aryl group, wherein $L_1$ and $L_2$ optionally contain at least one heteroatom with the proviso that when the heteroatom is oxygen, it cannot be bonded directly to G.

In another aspect, the present invention provides for a process for the hydrosilylation of a composition containing a silyl hydride and a compound containing at least one unsaturated group. The process includes the step of (i) contacting the composition with a metal complex of Formula (I), optionally in the presence of a solvent, to cause the silyl hydride to react with the compound containing at least one unsaturated group to produce a hydrosilylation product containing the metal complex, and (ii) optionally removing the metal complex from the hydrosilylation product.

DETAILED DESCRIPTION OF THE INVENTION

In one embodiment of the invention, there is provided a complex of the Formula (I)

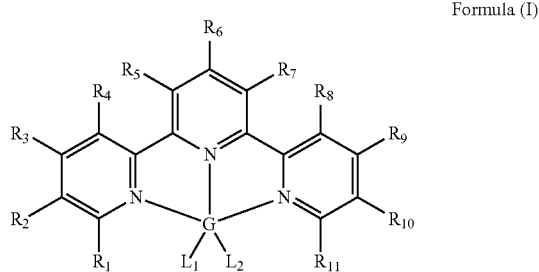

Formula (I)

In connection with this formula, G can be Mn, Fe, Ni, or Co in all the valence states. Preferably G is iron or cobalt. More preferably G is Fe, such as Fe (II) and Fe (III).

In Formula (I), $R_1$, $R_2$, $R_3$, $R_4$, $R_5$, $R_6$, $R_7$, $R_8$, $R_9$, $R_{10}$ and $R_{11}$ are independently hydrogen, C1-C18 alkyl, C1-C18 substituted alkyl, aryl, substituted aryl, or an inert functional group, wherein $R_1$-$R_{11}$, other than hydrogen, optionally contain at least one heteroatom; and wherein optionally $R_4$ and $R_5$ and/or $R_7$ and $R_8$ are joined together to form a ring being a substituted or unsubstituted, saturated, or unsaturated cyclic or polycyclic ring structure. In one embodiment, $R_6$ is aryl or substituted aryl, and $R_1$-$R_5$, $R_7$-$R_{11}$ are hydrogen. In another embodiment, $R_1$-$R_{11}$ are hydrogen.

Also in Formula (I), $L_1$ and $L_2$ are independently C1-C18 alkyl, C1-C18 substituted alkyl, aryl or substituted aryl group, wherein $L_1$ and $L_2$ optionally contain at least one heteroatom, with the proviso that when the heteroatom is oxygen, it cannot be bonded directly to G. In one embodiment, each of $L_1$ and $L_2$ is covalently bonded to G through a carbon atom. In another embodiment, $L_1$ and $L_2$ do not contain beta hydrogen. Typically, the alpha carbon refers to the carbon that attaches to G. By extension, the beta carbon refers to the carbon that attaches to the alpha carbon. As used herein, beta-hydrogen is meant the hydrogen attached to the beta carbon. Preferably, $L_1$ and $L_2$ are —$CH_2SiR^{20}{}_3$, wherein each occurrence of $R^{20}$ is C1-C18 alkyl, C1-C18 substituted alkyl, aryl or substituted aryl, preferably $R^{20}$ is a methyl group.

As used herein, "alkyl" includes straight, branched and cyclic alkyl groups. Specific and non-limiting examples of alkyls include, but are not limited to, methyl, ethyl, propyl and isobutyl.

By "substituted alkyl" herein is meant an alkyl group that contains one or more substituent groups that are inert under the process conditions to which the compound containing these groups is subjected. The substituent groups also do not substantially interfere with the process.

By "aryl" herein is meant a non-limiting group of any aromatic hydrocarbon from which one hydrogen atom has been removed. An aryl may have one or more aromatic rings, which may be fused, connected by single bonds or other groups. Specific and non-limiting examples of aryls include, but are not limited to, tolyl, xylyl, phenyl and naphthalenyl.

By "substituted aryl" herein is meant an aromatic group substituted as set forth in the above definition of "substituted alkyl." Similar to an aryl, a substituted aryl may have one or more aromatic rings, which may be fused, connected by single bonds or other groups; however, when the substituted aryl has a heteroaromatic ring, the free valence in the substituted aryl group can be to a heteroatom (such as nitrogen) of the heteroaromatic ring instead of a carbon. If not otherwise stated, it is preferred that substituted aryl groups herein contain 1 to about 30 carbon atoms.

By "inert functional group" herein is meant a group other than hydrocarbyl or substituted hydrocarbyl which is inert under the process conditions to which the compound containing the group is subjected. The inert functional groups also do not substantially interfere with any process described herein that the compound in which they are present may take part in. Examples of inert functional groups include halo (fluoro, chloro, bromo, and iodo), ether such as —$OR^{30}$ wherein $R^{30}$ is hydrocarbyl or substituted hydrocarbyl.

"Hetero atoms" herein is meant any of the Group 13-17 elements except carbon, and can include for example oxygen, nitrogen, silicon, sulfur, phosphorus, fluorine, chlorine, bromine, iodine, and combinations thereof.

Various methods can be used to prepare complexes of Formula (I). In one embodiment of the invention, there is provided a process for the synthesis of a complex of Formula (I). The process includes the step of reacting a complex of Formula (II) with at least one L containing alkylating agent selected from the group consisting of alkali metal salts, alkaline earth metal salts, Grignards, aluminum alkyls, mercury alkyls, thallium alkyls, and combinations thereof, wherein Formula (II) is:

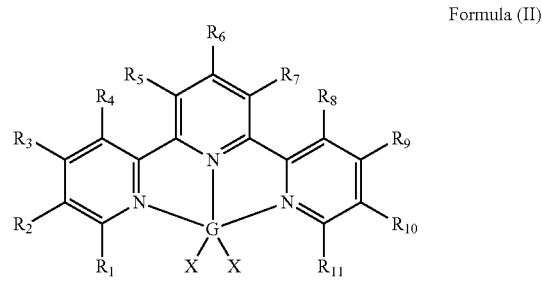

Formula (II)

wherein
G is Mn, Fe, Ni, or Co;
$R_1$, $R_2$, $R_3$, $R_4$, $R_5$, $R_6$, $R_7$, $R_8$, $R_9$, $R_{10}$ and $R_{11}$ are independently hydrogen, C1-C18 alkyl, C1-C18 substituted alkyl, aryl, substituted aryl, or an inert functional group, wherein $R_1$-$R_{11}$, other than hydrogen, optionally contain at least one heteroatom; and wherein optionally $R_4$ and $R_5$ and/or $R_7$ and $R_3$ are joined together to form a ring being a substituted or unsubstituted, saturated, or unsaturated cyclic or polycyclic ring structure;

X is an anion such as F, Cl, Br, I, $CF_3R^{40}SO_3^-$ or $R^{50}COO^-$, wherein $R^{40}$ is a covalent bond or a C1-C6 alkyl group, and $R^{50}$ is a C1-C10 hydrocarbyl group; and each occurrence of L is independently C1-C18 alkyl, C1-C18 substituted alkyl, aryl or substituted aryl group. In some embodiments, L optionally contains at least one heteroatom.

As used herein, alkali metal salts include for example monoalkyl salts of lithium, sodium, potassium, rubidium and cesium. Alkaline earth metal salts include for example dialkyl salts of beryllium, magnesium, calcium, strontium and barium. Grignards suitable for the present invention include alkyl magnesium halides. Aluminum alkyls include for example trialkyl aluminum salts. Mercury alkyls refer to dialkyl mercury salts. Thallium alkyls include monoalkyl and trialkyl thallium salts.

The metal complexes disclosed herein are useful as catalysts for hydrosilylation reactions. When used as a catalyst, the complexes of Formula (I) can be unsupported or immobilized on a support material, for example, carbon, silica, alumina, $MgCl_2$, zirconia, or on a polymer or prepolymer, for example polyethylene, polypropylene, polystyrene, or poly (aminostyrene). The metal complexes can also be supported on dendrimers.

In some embodiments, for the purposes of attaching the metal complexes of the invention to a support, it is desirable that at least one of $R_1$ to $R_{11}$ of the metal complexes, preferably $R_6$, has a functional group which is effective to covalently bond to the support. Exemplary functional groups include but are not limited to SH, COOH, $NH_2$ or OH groups.

In one embodiment, silica supported catalyst may be prepared via Ring-Opening Metathesis Polymerization (ROMP) technology as discussed in the literature, for example Macromol. Chem. Phys. 2001, 202, No. 5, pages 645-653; Journal of Chromatography A, 1015 (2003) 65-71.

One way to immobilize catalysts on the surface of dendrimers is by the reaction of Si—Cl bonded parent dendrimers and functionalized terpyridine in the presence of a base as illustrated by Kim et al. in Journal of Organometallic Chemistry 673 (2003) 77-83.

In one embodiment, the complexes of Formula (I) are used as catalysts for the hydrosilylation of a composition containing a silyl hydride and a compound having at least one unsaturated group. The process includes contacting the composition with a metal complex of Formula (I), either supported or unsupported, to cause the silyl hydride to react with the compound having at least one unsaturated group to produce a hydrosilylation product which may contain the metal complex catalyst. The hydrosilylation reaction can be conducted optionally in the presence of a solvent. If desired, when the hydrosilylation reaction is completed, the metal complex can be removed from the reaction product by magnetic separation and/or filtration.

By "unsaturated" is meant one or more double or triple bonds. In a preferred embodiment, it refers to carbon-carbon double or triple bonds.

The silyl hydride employed in the hydrosilylation reaction is not particularly limited. It can be any compound selected from the group consisting of $R_aSiH_{4-a}$, $(RO)_aSiH_{4-a}$, $Q_uT_vT_p^HD_wD^H_xM^H_yM_z$, and combinations thereof. The silyl hydride can contain linear, branched or cyclic structures, or combinations thereof. As used herein, each occurrence of R is independently C1-C18 alkyl, C1-C18 substituted alkyl, wherein R optionally contains at least one heteroatom, each occurrence of a independently has a value from 1 to 3, each of u, v, p, y and z independently has a value from 0 to 20, each of w and x independent has a value from 0 to 500, provided that p+x+y equals 1 to 500, and the valences of the all the elements in the silyl hydride are satisfied. Preferably, u, v, p, y, and z each independently has a value from 0 to 10, w and x each independently has a value from 0 to 100, and p+x+y equals 1 to 100.

As used herein, an "M" group represents a monofunctional group of formula $R'_3SiO_{1/2}$, a "D" group represents a difunctional group of formula $R'_2SiO_{2/2}$, a "T" group represents a trifunctional group of formula $R'SiO_{3/2}$, and a "Q" group represents a tetrafunctional group of formula $SiO_{4/2}$, an "$M^H$" group represents $H_gR'_{3-g}SiO_{1/2}$, a "$T^H$" represents $HSiO_{3/2}$, and a "$D^H$" group represents $R'HSiO_{2/2}$. As used herein, g is from 0 to 3. Each occurrence of R' is independently C1-C18 alkyl, C1-C18 substituted alkyl, wherein R' optionally contains at least one heteroatom.

The compound containing an unsaturated group employed in the hydrosilylation reaction includes, but is not limited to, unsaturated polyethers such as alkyl-capped allyl polyethers, vinyl functionalized alkyl capped allyl or methylallyl polyethers; terminally unsaturated amines; alkynes; C2-C18 olefins, preferably alpha olefins; unsaturated cycloalkyl epoxides such as vinyl cyclohexane epoxide; terminally unsaturated acrylates or methyl acrylates; unsaturated aryl ethers; unsaturated aromatic hydrocarbons; unsaturated cycloalkanes such as trivinyl cyclohexane; vinyl-functionalized polymers; vinyl-functionalized silanes and vinyl-functionalized silicones.

Unsaturated polyethers suitable for the hydrosilylation reaction preferably are polyoxyalkylenes having the general formula:

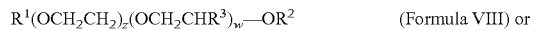

$R^1(OCH_2CH_2)_z(OCH_2CHR^3)_w$—$OR^2$ (Formula VIII) or

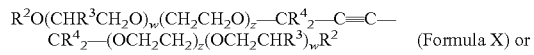

$R^2O(CHR^3CH_2O)_w(CH_2CH_2O)_z$—$CR^4_2$—$C\equiv C$—
$CR^4_2$—$(OCH_2CH_2)_z(OCH_2CHR^3)_wR^2$ (Formula X) or

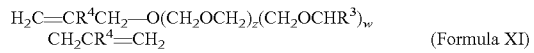

$H_2C=CR^4CH_2$—$O(CH_2OCH_2)_z(CH_2OCHR^3)_w$
$CH_2CR^4=CH_2$ (Formula XI)

wherein $R^1$ denotes an unsaturated organic group containing from 2 to 10 carbon atoms such as allyl, methylallyl, propargyl or 3-pentynyl. When the unsaturation is olefinic, it is desirably terminal to facilitate smooth hydrosilylation. However, when the unsaturation is a triple bond, it may be internal. $R^2$ is hydrogen, vinyl, or a polyether capping group of from 1 to 8 carbon atoms such as the alkyl groups: $CH_3$, n-$C_4H_9$, t-$C_4H_9$ or i-$C_8H_{17}$, the acyl groups such as $CH_3COO$, t-$C_4H_9COO$, the beta-ketoester group such as $CH_3C(O)CH_2C(O)O$, or a trialkylsilyl group. $R^3$ and $R^4$ are monovalent hydrocarbon groups such as the C1-C20 alkyl groups, for example, methyl, ethyl, isopropyl, 2-ethylhexyl, dodecyl and stearyl, or the aryl groups, for example, phenyl and naphthyl, or the alkaryl groups, for example, benzyl, phenylethyl and nonylphenyl, or the cycloalkyl groups, for example, cyclohexyl and cyclooctyl. $R^4$ may also be hydrogen. Methyl is the most preferred $R^3$ and $R^4$ groups. Each occurrence of z is 0 to 100 inclusive and each occurrence of w is 0 to 100 inclusive. Preferred values of z and w are 1 to 50 inclusive.

The metal complexes of Formula (I) are useful for catalyzing various industrially practiced hydrosilylation reactions. For example, these complexes can be used in the reactions involving (1) the crosslinking of silicone hydride fluids with terminally unsaturated polymers, and (2) hydrosilylation of allyl amines with tertiary silanes. Accordingly, the metal complexes of the invention have utility in the preparation of useful silicone products, including, but are not limited to, coatings, for example release coatings, room temperature vulcanizates, sealants and adhesives, products for agricultural and personal care applications, and silicone surfactants for stabilizing polyurethane foams.

When used as a catalyst for hydrosilylation reactions, the metal complexes of the invention are efficient and selective. For example, when the metal complexes of the invention are employed in the hydrosilylation of an alkyl-capped allyl polyether and a compound containing an unsaturated group, the reaction products are essentially free of unreacted alkyl-capped allyl polyether and its isomerization products. In one embodiment, the reaction products do not contain the unreacted alkyl-capped allyl polyether and its isomerization products. Further, when the compound containing an unsaturated group is an unsaturated amine compound, the hydrosilylation product is essentially free of internal addition products, unreacted unsaturated amine, and the isomerization products of the unsaturated amine compound. As used herein, "essentially free" is meant no more than 10%, preferably no more than 5% based on the total weight of the hydrosilylation product. "Essentially free of internal addition products" is meant that silicon is added to the terminal carbon.

The following examples are intended to illustrate, but in no way limit the scope of the present invention. All parts and percentages are by weight and all temperatures are in degrees Celsius unless explicitly stated otherwise. All the publications and US patents referred to in the application are hereby incorporated by reference in their entireties.

EXAMPLES

General Considerations

All air- and moisture-sensitive manipulations were carried out using standard vacuum line, Schlenk, and cannula techniques or in an MBraun inert atmosphere drybox containing an atmosphere of purified nitrogen. Solvents for air- and moisture-sensitive manipulations were initially dried and deoxygenated using literature procedures. See for example Pangborn et al., J. Organometallics 1996, 15, 1518.

The following abbreviations and terms are used:
bs—broad singlet
s—singlet
t—triplet
bm—broad multiple
GC—Gas Chromatograph
MS—Mass Spectroscopy
THF—tetrahydrofuran Example 1

Preparation of Iron (II) Terpyridine Dichloride

In an inert atmosphere, a scintillation vial was charged with 0.233 g (1.0 mmol) of terpyridine and 0.126 g (1.0 mmol) of ferrous dichloride. Approximately 20 mL of dry THF was added to the mixture and the resulting slurry was stirred overnight. Then approximately 50 mL of pentane was added resulting in precipitation of a purple solid. The solid was collected and dried in vacuo to yield 0.345 g (96%) of the iron (II) terpyridine dichloride. The sample was compared to previously reported compound. See Reiff, William M.; Erickson, N. E.; Baker, Willie Arthur, Jr. Mono(2,2',2"-terpyridine) complexes of iron(II). Inorganic Chemistry (1969), 8(9), 2019-21.

Example 2

Preparation of Bis[(trimethylsilyl)methyl]iron(II)terpyridine

In an inert atmosphere, a round bottomed flask was charged with 0.360 g (1.0 mmol) of terpyridine iron dichloride, and approximately 10 mL of diethyl ether. The flask was chilled to −35° C. A solution containing 0.188 g (2.0 mmol) of LiCH$_2$SiMe$_3$ was added followed by approximately 10 mL of diethyl ether. A color change occurred immediately upon addition and the resulting slurry was stirred and allowed to warm to ambient temperature. After stirring for one hour, the reaction mixture was filtered through Celite® and the volatiles were removed in vacuo. The resulting paramagnetic purple solid was washed with approximately 5 mL of cold pentane yielding 0.400 g (87%) of the title compound. $^1$H NMR (benzene-d$_6$, 20° C.): δ=319.80 (bs, 1H), 194.68 (bs, 2H), 154.65 (bs, 2H), 115.20 (bs, 2H), 59.36 (bs, 2H), 38.56 (bs, 2H), 8.73 (bs, 18H).

Example 3

Hydrosilylation of 1-hexene with Et$_3$SiH using Bis[(trimethylsilyl)methyl]iron(II)terpyridine catalyst A stock solution containing 5 mg of bis[(trimethylsilyl)methyl]iron(II) terpyridine and 0.60 g of toluene was charged into a scintillation vial in a nitrogen filled drybox. The toluene was removed in vacuo followed by addition of 0.114 g (1.4 mmol) of 1-hexene. To the same vial, 0.105 g (0.90 mmol) of Et$_3$SiH was added. The vial was sealed with a small amount Krytox grease and electrical tape, removed from the drybox and placed in a 95° C. oil bath. The concentration of the iron complex was less than 0.1 mol % relative to the silane, and the reaction time was 4 hours to achieve greater than 90% conversion to (CH$_3$CH$_2$)$_3$Si—(CH$_2$)$_5$—CH$_3$. Less than 5% each of (CH$_3$CH$_2$)$_3$Si—CH=CH—(CH$_2$)$_3$—CH$_3$ and (CH$_3$CH$_2$)$_2$ (H)Si—(CH$_2$)$_5$—CH$_3$ were formed.

To perform the reaction in a solvent such as toluene, the above procedure was carried out without removal of the solvent from the stock solution. The conversion was monitored by GC/MS.

Example 4

Hydrosilylation of 1-Octene with Methylbis(trimethylsilyloxy)silane (MD$^H$M) using Bis[(trimethylsilyl)methyl]iron(II)terpyridine In an inert atmosphere, to a scintillation vial was added 0.150 g (1.33 mmol) of 1-octene and 0.295 g (1.33 mmol) of MD$^H$M. To this stirring solution was added 0.015 g (2.5 mol %) Bis[(trimethylsilyl)methyl]iron(II) terpyridine. The reaction was sealed and moved to an oil bath, and held at about 60° C. for approximately one hour. The resonance associated with the Si—H in the $^1$H NMR was observed to disappear during the course of the reaction, and a new resonance upfield at 0.41 ppm assignable to methylene attached to silicon appeared, giving a spectrum consistent with that of the previously reported compound.

Gas chromatography was performed on a Shimadzu GC-2010 gas chromatograph. GC analyses were performed using a Supelco 30 m×0.25 mm BETA DEX 120 capillary column. Temperature program for the reaction of MD$^H$M and 1-octene was as follows: 80° C., 2 min.; 15° C./min to 180° C., 2 min. The retention time of the hydrosilylated product was 7.83 minutes.

Example 5

Hydrosilylation of Vinylcyclohexene Oxide (VCHO) with Methylbis(trimethylsilyloxy)silane ($MD^HM$) using Bis[(trimethylsilyl)methyl]iron(II)terpyridine In an inert atmosphere, to a scintillation vial was added 0.150 g (1.33 mmol) of VCHO and 0.295 g (1.33 mmol) of $MD^HM$. To this stirring solution was added 0.015 g (2.5 mol %) Bis[(trimethylsilyl)methyl]iron(II) terpyridine. The vial was sealed; and the reaction was run at around 60° C. for about 1 hour. The resonances associated with the Si—H and $CH_2$=CH in the $^1H$ NMR were observed to disappear during the course of the reaction, and a new resonance upfield at 0.37 ppm assignable to methylene attached to silicon appeared, which was indicative of formation of the desired product.

Example 6

Cross linking reaction of Si—H and Si-vinyl siloxanes with Bis[(trimethylsilyl)methyl]iron(II)terpyridine catalyst To a scintillation vial in a nitrogen filled drybox was added 3 mg (0.0065 E-3 mmol) Bis[(trimethylsilyl)methyl]iron(II) terpyridine. 400 mg of a vinyl end-stopped siloxane polymer of the structure $M^{vi}D_{120}M^{vi}$, in which $M^{vi}$=vinyl dimethyl $SiO_{2/2}$, was then added, followed by 18 mg of a hydride-functional siloxane polymer of the structure $MD_{15}D^H{}_{30}M$. The vial was sealed with a small amount of Krytox grease, electrical tape, removed from the drybox and placed in a 95° C. oil bath for 12 hours. The reaction was cooled in air and yielded a highly viscous semi-solid. This reaction was 0.7% by mass iron compound and 0.0009% iron by mass on a wt/wt basis of the total amount of starting materials in the reaction.

Comparative Examples

Attempted Hydrosilylations Using (Bipyridine)Iron Complex

To a scintillation vial in a nitrogen filled drybox was added 10 mg (0.0052 mmol) of Bis[(trimethylsilyl)methyl]iron(II) 2,2'-Bipyridine. 1-Hexene was then added (0.114 g, 1.4 mmol), followed by 0.105 g (0.90 mmol) of $Et_3SiH$. The vial was sealed with a small amount of Krytox grease, electrical tape, removed from the drybox and placed in a 95° C. oil bath for 12 hours. No conversion to products was observed as judged by GC.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A complex according to Formula (I) wherein the complex is immobilized on a support, wherein the Formula (I) is

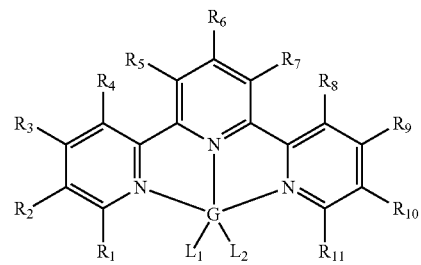

Formula (I)

Wherein:
G is Mn, Fe, Ni or Co;
$R_1$, $R_2$, $R_3$, $R_4$, $R_5$, $R_6$, $R_7$, $R_8$, $R_9$, $R_{10}$ and $R_{11}$ are independently hydrogen, C1-C18 alkyl, C1-C18 substituted alkyl, aryl or substituted aryl group, or an inert functional group, wherein $R_1$-$R_{11}$, other than hydrogen, optionally contain at least one heteroatom; and wherein optionally $R_4$ and $R_5$ and/or $R_7$ and $R_8$ are joined together to form a ring being a substituted or unsubstituted, saturated, or unsaturated cyclic or polycyclic ring structure; and
$L_1$ and $L_2$ are independently C1-C18 alkyl, C1-C18 substituted alkyl, aryl, substituted aryl, wherein $L_1$ and $L_2$ optionally contain at least one heteroatom, with the proviso that when the heteroatom is oxygen, it cannot be bonded directly to G.

2. The complex of claim 1 wherein the support is selected from the group consisting of carbon, silica, alumina, $MgCl_2$, zirconia, polyethylene, polypropylene, polystyrene, poly (aminostyrene), dendrimers, and combinations thereof.

3. The complex of claim 1 wherein at least one of $R_1$-$R_{11}$ contains at least one functional group that covalently bonds with the support.

4. A process for the hydrosilylation of a composition containing a silyl hydride and a compound containing at least one unsaturated group, the process comprising: (i) contacting the composition with the complex of Formula (I), optionally in the presence of a solvent, to cause the silyl hydride to react with the compound containing at least one unsaturated group to produce a hydrosilylation product containing said complex, and (ii) optionally removing the complex from the hydrosilylation product, wherein the Formula (I) is

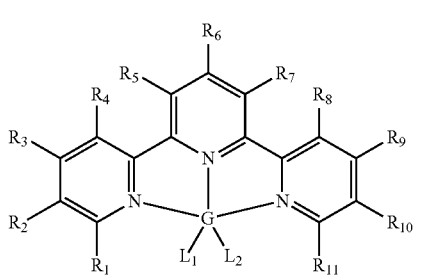

Formula (I)

wherein:
G is Mn, Fe, Ni or Co;
$R_1$, $R_2$, $R_3$, $R_4$, $R_5$, $R_6$, $R_7$, $R_8$, $R_9$, $R_{10}$ and $R_{11}$ are independently hydrogen, C1-C18 alkyl, C1-C18 substituted alkyl, aryl or substituted aryl group, or an inert functional group, wherein $R_1$-$R_{11}$, other than hydrogen, optionally contain at least one heteroatom; and wherein optionally $R_4$ and $R_5$ and/or $R_7$ and $R_8$ are joined together to form a ring being a substituted or unsubstituted, saturated, or unsaturated cyclic or polycyclic ring structure; and $L_1$ and $L_2$ are independently C1-C18 alkyl, C1-C18 substituted alkyl, aryl, substituted aryl, wherein $L_1$ and $L_2$ optionally contain at least one heteroatom, with the proviso that when the heteroatom is oxygen, it cannot be bonded directly to G.

5. The process of claim 4 comprising the step of removing the complex from the hydrosilylation product by magnetic separation and/or filtration.

6. The process of claim 4 wherein the complex is immobilized on a support.

7. The process of claim 4 wherein the support is selected from the group consisting of carbon, silica, alumina, $MgCl_2$, zirconia, polyethylene, polypropylene, polystyrene, poly(aminostyrene), dendrimers, and combinations thereof.

8. The complex of claim 4 wherein at least one of $R_1$-$R_{11}$ contains at least one functional group that covalently bonds with the support.

9. The process of claim 4, wherein the silyl hydride is selected from the group consisting of $R_aSiH_{4-a}$, $(RO)_aSiH_{4-a}$, $Q_uT_vT_p^HD_wD^H_xM^H_yM_z$, and combinations thereof, wherein Q is $SiO_{4/2}$, T is $R'SiO_{3/2}$, $T^H$ is $HSiO_{3/2}$, D is $R'_2SiO_{2/2}$, $D^H$ is $R'HSiO_{2/2}$, $M^H$ is $H_gR'_{3-g}SiO_{1/2}$, M is $R'_3SiO_{1/2}$, each occurrence of R and R' is independently C1-C18 alkyl, C1-C18 substituted alkyl, wherein R and R' optionally contain at least one heteroatom, each occurrence of a independently has a value from 1 to 3, g has a value of from 0 to 3, p is from 0 to 20, u is from 0 to 20, v is from 0 to 20, w is from 0 to 500, x is from 0 to 500, y is from 0 to 20, and z is from 0 to 20, provided that p+x+y equals 1 to 500, and the valences of the all the elements in the silyl hydride are satisfied.

10. The process of claim 4, wherein p, u, v, y, and z are from 0 to 10, w and x are from 0 to 100, wherein p+x+y equals 1 to 100.

11. The process of claim 4, wherein the compound containing an unsaturated group is selected from the group consisting of an alkyl-capped allyl polyether, a vinyl functionalized alkyl-capped allyl or methylallyl polyether, a terminally unsaturated amine, an alkyne, a C2-C18 olefin, an unsaturated cycloalkyl epoxide, a terminally unsaturated acrylate or methyl acrylate, an unsaturated aryl ether, an unsaturated aromatic hydrocarbon, an unsaturated cycloalkane, a vinyl-functionalized polymer, a vinyl-functionalized silane, a vinyl-functionalized silicone, and combinations thereof.

12. The process of claim 4, wherein the compound containing an unsaturated group is a polyoxyalkylene having the generic formula:

 (Formula VIII) or

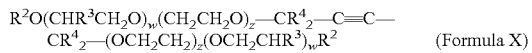

(Formula X)

or

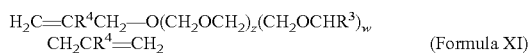

(Formula XI)

wherein each occurrence of $R^1$ is an unsaturated organic group containing from 2 to 10 carbon atoms, each occurrence of $R^2$ is independently hydrogen, vinyl, or a poly-ether capping group of from 1 to 8 carbon atoms, each occurrence of $R^3$ and $R^4$ are independently monovalent hydrocarbon groups, each occurrence of z is 0 to 100 inclusive, and each occurrence of w is 0 to 100 inclusive.

13. A composition produced from the process of claim 4 wherein the compound containing an unsaturated group is an alkyl-capped allyl polyether; wherein the composition contains the complex of the Formula (I), and wherein the composition is essentially free of unreacted alkyl-capped allyl polyether and its isomerization products.

14. A composition produced from the process of claim 4 wherein the compound containing an unsaturated group is a terminally unsaturated amine, wherein the composition contains the complex of the Formula (I) and wherein the composition is free of unreacted terminally unsaturated amine and its isomerization products, and wherein the product is essentially free of internal addition products.

15. A composition produced from the process of claim 4 wherein the compound containing at least one unsaturated group is a vinyl-functionalized silicone, and wherein the composition contains the complex of the Formula (I).

16. A process for the synthesis of a complex of Formula (I) comprising the step of reacting a complex of Formula (II) with at least one L-containing alkylating agent selected from the group consisting of alkali metal salts, alkaline earth metal salts, Grignards, aluminum alkyls, mercury alkyls, thallium alkyls, and combinations thereof, wherein the Formula (II) is

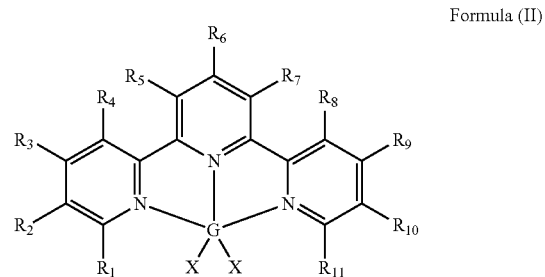

Formula (II)

wherein

G is Mn, Fe, Ni, or Co;

$R_1$, $R_2$, $R_3$, $R_4$, $R_5$, $R_6$, $R_7$, $R_8$, $R_9$, $R_{10}$ and $R_{11}$ are independently hydrogen, C1-C18 alkyl, C1-C18 substituted alkyl, aryl, substituted aryl, or an inert functional group, wherein $R_1$-$R_{11}$, other than hydrogen, optionally contain at least one heteroatom; and wherein optionally $R_4$ and $R_5$ and/or $R_7$ and $R_8$ are joined together to form a ring being a substituted or unsubstituted, saturated, or unsaturated cyclic or polycyclic ring structure; and X is F, Cl, Br, I, $CF_3R^{40}SO_3^-$ or $R^{50}COO^-$, wherein $R^{40}$ is a covalent bond or a C1-C6 alkyl group, and $R^{50}$ is a C1-C10 hydrocarbyl group; and wherein each occurrence of L is independently C1-C18 alkyl, C1-C18 substituted alkyl, aryl or substituted aryl group, wherein L optionally contains at least one heteroatom.

* * * * *